United States Patent
Biaggio et al.

(10) Patent No.: US 7,951,842 B2
(45) Date of Patent: May 31, 2011

(54) USE OF CUPUASSU BUTTER BASED AMPHOTERIC AMIDOAMINES AS AMPHOTERIC SURFACTANTS

(75) Inventors: Rosa Maria Teixeira Tagé Biaggio, São José dos Campos (BR); Setsuo Sato, São Jose dos Campos (BR); Juliana Bucchi Alencastre, São José dos Campos (BR); Carlos Alberto Moura, Jacarei (BR); Henrique Sales, São José dos Campos (BR); Tiago Costa Beber, São Paulo (BR); Rosa Maria da Cunha Canto Friedlander, São Paulo (BR); Tereza Maria de Senne Peranovich Victorio, São Paulo (BR); Edjane dos Santos Lima, São Paulo (BR)

(73) Assignees: Cognis Brasil Ltda., Sao Paulo (BR); Natura Cosmeticos S.A., Itapecerica da Serra (BR)

( * ) Notice: Subject to any disclaimer, the term of this patent is extended or adjusted under 35 U.S.C. 154(b) by 0 days.

(21) Appl. No.: 11/575,019

(22) PCT Filed: Sep. 9, 2005

(86) PCT No.: PCT/BR2005/000181
§ 371 (c)(1),
(2), (4) Date: Jan. 17, 2008

(87) PCT Pub. No.: WO2006/026843
PCT Pub. Date: Mar. 16, 2006

(65) Prior Publication Data
US 2008/0167494 A1    Jul. 10, 2008

(30) Foreign Application Priority Data

Sep. 9, 2004 (BR) .................................... 0403781

(51) Int. Cl.
*A61K 31/205* (2006.01)
*A61K 8/02* (2006.01)
*C07C 229/00* (2006.01)
(52) U.S. Cl. .................... 514/556; 424/401; 554/107
(58) Field of Classification Search ............... None
See application file for complete search history.

(56) References Cited

U.S. PATENT DOCUMENTS
4,497,825 A * 2/1985 Bade ........................ 514/556
5,354,906 A 10/1994 Weitemeyer et al.

FOREIGN PATENT DOCUMENTS
GB    2 321 061 A    7/1998
JP    2002 348226 A    12/2002

* cited by examiner

*Primary Examiner* — Paul A Zucker
(74) *Attorney, Agent, or Firm* — Alston & Bird LLP

(57) ABSTRACT

This invention relates to the use of compounds of the general formula (I): $R^1$—CONH—X—$NR^2R^3$—$R^4$—Y in which $R^1$ represents an alkyl moiety containing 11 to 21 carbon atoms, X stands for a $(CH_2)_n$- group and n is an integer from 1 to 6, $R^2$ and $R^3$ independently represent an alkyl moiety with 1 to 4 carbon atoms or an hydrogen atom, Y stands for a COO— group, in cosmetic compositions, characterized in that the compound of formula (I): is prepared by reacting the oil from Theo-broma grandiflorum with an amine of the formula (II): $H^2N$—X—$NR^2R^3$ and subsequently reaction with sodium monochloroacetic acid.

14 Claims, 2 Drawing Sheets

USE OF CUPUASSU BUTTER BASED AMPHOTERIC AMIDOAMINES AS AMPHOTERIC SURFACTANTS

FIELD AND BACKGROUND OF THE INVENTION

The present invention is directed towards the use of selected amidoamines in cosmetic compositions.

Compounds classified as "amphoteric surfactants" are an important class of surfactants. Best known and widely used are the so-called alkylamido betaines, especially cocamido propyl betaine. These betaines are extensively used in personal care products, as shampoos, bubble baths and other cleansing products, because they are considered as being very mild while having high foaming capacities. Nevertheless, they are still irritant to the eyes and sensitive skin.

SUMMARY OF THE INVENTION

It was the aim of the present invention to provide amphoteric surfactants with enhanced softening and mildness properties, which also exhibit a viscosity increasing effect.

DETAILED DESCRIPTION

Figure 1:
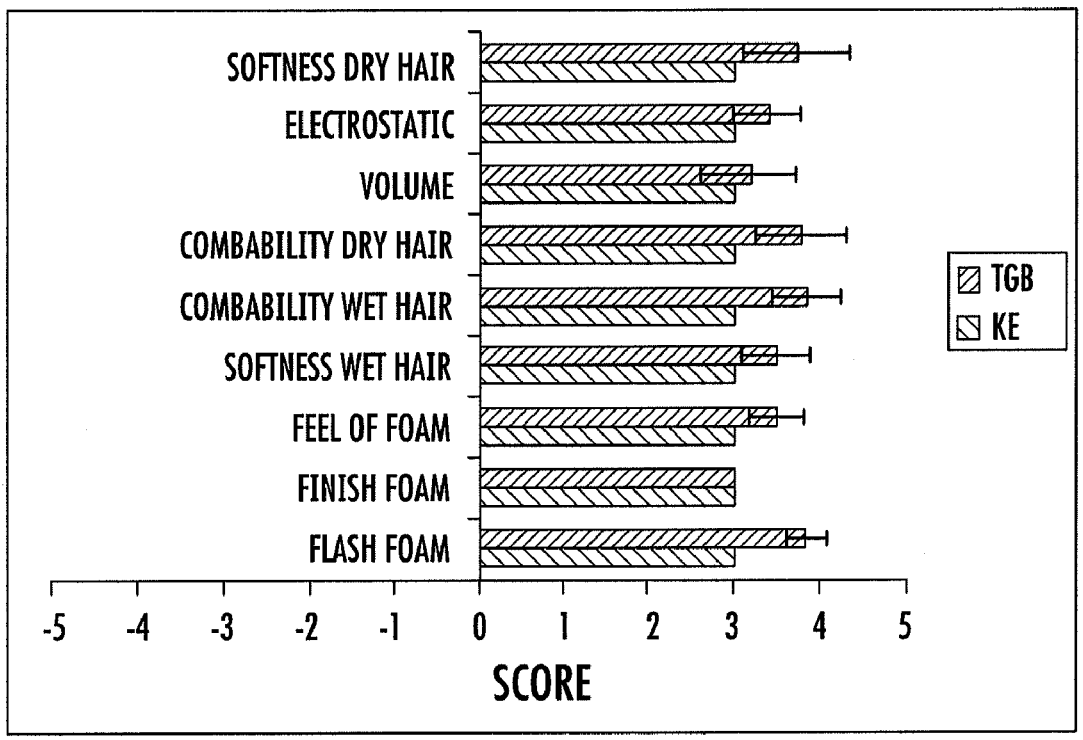
FIG. 1 is a bar graph comparing the difference between shampoo formulations.

A first embodiment of the present invention therefore relates to the use of compounds of the general formula (I)

$$R^1—CONH—X—NR^2R^3—R^4—Y \quad (I)$$

in which $R^1$ represents an alkyl moiety containing 11 to 21 carbon atoms, X stands for a $(CH_2)_n$— group and n is an integer from 1 to 6, $R^2$ and $R^3$ independently represent an alkyl moiety with 1 to 4 carbon atoms or an hydrogen atom, Y stands for a COO— group, in cosmetic compositions, characterized in that the compound of formula (I) is prepared by reacting the oil from Theobroma grandiflorum with an amine of the formula (II)

$$H_2N—X—NR^2R^3 \quad (II)$$

and subsequently reaction with sodium monochloroacetic acid. The final product is amphoteric, which means that it contains an acidic and a basic moiety. This is often called a betaine. Compounds of the general formula (I) are known. They are so called amidoamines, which can be prepared by reacting a carboxylic acid with a di-functional amine and subsequently reacting the resulting product with a quaternizing agent, preferably a chloroacetic acid. Methods for preparation of such compounds can be found for example in DE 43 40 423 C1, DE 42 07 386 C1 and DE 44 30 084 A1 respectively. The compounds of the present invention are distinguished from the compounds known in the art by the source of carboxylic acids, which is the oil of Theobroma grandflorum, a tree from the Amazon forest. Another name for this oil is Cupuassu butter. Cupuassu is a tree from the Amazon forest, growing in dry land. It grows up to 20 meters high. The fruit is an ellipsoid berry, weighing up to 1.5 kg. Inside of it, there are the oleaginous seeds, surrounded by a white mass, very similar to cocoa. The fructification happens from January to May. The fruit peel are removed and the seeds are pressed for removing the butter. Typically, Cupuassu butter contains phytosterols and a mixture of fatty acids having 14, 16, 18 (stearic, oleic, linoleic and linolenic acid), 20 and 22 carbon atoms in which oleic acid, followed by stearic acid and arachidonic acid are the main components. However, the sterol content is very low, in the oil typically only 1% by weight is the sterol fraction. A detailed analysis of Cupuassu butter is given in the following table:

| Cupuassu butter | |
| --- | --- |
| Appearance @ 25° C. | Solid |
| Colour | White and yellowish |
| Iodine value (gl2/100 g) | 40-50 |
| Saponification value (mgKOH/g) | 180-200 |
| Acid Value (mgKOH/g) | Max. 10.0 |
| Insaponificable (%) | max. 3.0 |
| Peroxide value (meq/kg) | max. 10 |

| Fatty Acid distribution | |
| --- | --- |
| Miristic acid (C14, %) | 0.0-1.0 |
| Palmitic Acid (C16, %) | 5.0-10.0 |
| Stearic Acid (C18, %) | 25.0-35.0 |
| Oleic Acid (C18:1, %) | 30.0-50.0 |
| Linoleic Acid (C18:2, %) | 2.0-5.0 |
| Linolenic Acid (C18:3, %) | 0.0-1.0 |
| Araquidonic Acid (C20:0, %) | 10.0-15.0 |
| Behenic Acid (C22:0, %) | 0.0-3.0 |

This very unique distribution of carboxylic acids in the Cupuassu butter is essential for the present invention. The preparation of Cupuassu butter is described, for instance, in EP 1 219 698 A1, see especially the examples on pages 7 to 9 of this application.

The preparation of the compounds of the present invention is described below: The preparation is conducted preferably in a two-step process: in the first step the Cupuassu butter—their glycerides or methyl esters—are reacted with dimethylaminopropyl amine. The reaction takes place in a temperature range from 140° C. up to 210° C., and needs approximately four hours. The resulting amido amide is washed to eliminate any excess of amine. In the second step the amidoamine of the Cupuassu butter triglycerides reacts with a quaternizing compounds, preferably sodium monochloroacetate. The reaction can be understood as a quaternization reaction of a tertiary amine with a monochloroacetate as an alkylating agent. A high degree of conversion occurs if during the alkylation process a salt is formed with monochloroacetate, because the free acid would hinder the amine function. Therefore, weakly alkaline conditions, analogous to the dissociation degree of monochloroacetic acid, are recommended. Also, a slight excess of monochloroacetate increases the yield. The reaction is carried out in an aqueous solution, and the amidoamine of Cupuassu butter from the first step is added at 80-85° C. Then the temperature is kept at 80-85° C. for three hours. During the reaction, it is preferred to add each hour the corresponding amount of NaOH. This limits the amount of undesired by-products. The pH during the reaction should be maintained at a value between 8 and 9. The final product is yielded in a concentration of 20% by weight up to at maximum 50% by weight of betain. The sterol content of the final product is at maximum 1000 ppm.

It is preferred to use such compounds according to formula (I) in which $R^2$ is identically to $R^3$. It is further preferred to use those compounds of formula (I) in which both $R^2$ and $R^3$ represents an alkyl moiety, preferably a methyl group. It is advantageous to select compounds of formula (I), containing as group X a $(CH_2)_3$-group.

The compounds according to the present invention can be used as amphoteric surfactants in cosmetic compositions, especially for cutaneous and capillary treatment. The compound promotes excellent softness and mildness to skin and hair while exhibiting high-foam performance.

Generally, the cosmetic compositions according to the invention contain 0.1 to 20% bei weight of the compound of general formula (I). The compound of general formula (I) can be used in cosmetic compositions in the same way as Cocamido propyl betaine.

EXAMPLES

Half Head Tests

The following two compositions A and B were used for the half head test on 10 women (age 20-35) with coloured or chemically treated hair. The hair was washed for 2 minutes and afterwards treated on the left half head with formulation B (based on Cocamidopropyl betaine) and on the right half head with formulation A (based on Cupuassuamidopropyl betaine).

| Composition | A (%) | B (%) |
|---|---|---|
| Phase I | | |
| Sodium Laureth Sulfate | 37.00 | 37.00 |
| Cupuassuamido propyl betaine | 1.50 | — |
| Cocamido propyl betaine | — | 1.50 |
| Water | ad 100 | |
| PEG-150 Distearate | 0.50 | 0.50 |
| Phase II | | |
| Glycol Distearate | 2.50 | 2.50 |
| Phase III | | |
| Guar Hydroxypropyl trimonium chloride | 0.20 | 0.20 |
| Water | 10.00 | 10.00 |
| Phase IV | | |
| 5-Chloro-2-methyl-4-isothiazolin-3-one (and) 2-Methyl-4-isothiazolin-3-one | 0.20 | 0.20 |
| NaCl | 1.40 | 1.60 |

Method of Preparation:

1. Components of phase I with the exception of PEG-150 Distearate were homogenized and heated to 75° C. Then PEG-150 Distearate was added and the mixture was homogenized again.

2. Phase II was heated to 75° C.

3. Phase II was added to Phase I under agitation.

4. Guar Hydroxypropyl trimonium chloride was dispersed in water. Citric acid was added to a pH value of 3.0 to 4.0.

5. When the combined phases II and I had cooled down to 30° C., phase III and phase IV are added. The pH value is adjusted to 5.5 to 6.5 and the composition is homogenized.

The following rating system for evaluating the different parameters was used:
  0=Identical
  ±1.0=minor difference, only detectable by half head test;
  ±2.0=slightly great difference, only detectable by half head test;
  ±3.0=greater difference
  ±4.0=difference detectable from experts;
  ±5.0=distinct difference FIG. 1 shows the results for the half head test in which TGB=Formulation A, KE=Formulation B. The shampoo containing cupuassuamido propyl betaine instead of cocamido propyl betaine is superior with regard to combability, softness and conditioning of hair as well as foam properties.

Foam Test 2 g of shampoo composition A or B were diluted with water to a concentration of 1% with regard to the shampoo and this solution was shaken 30 times in a 1000 ml measuring cylinder. The foam level was measured directly after shaking as well as after 5 and 15 min respectively.

Figure 2:
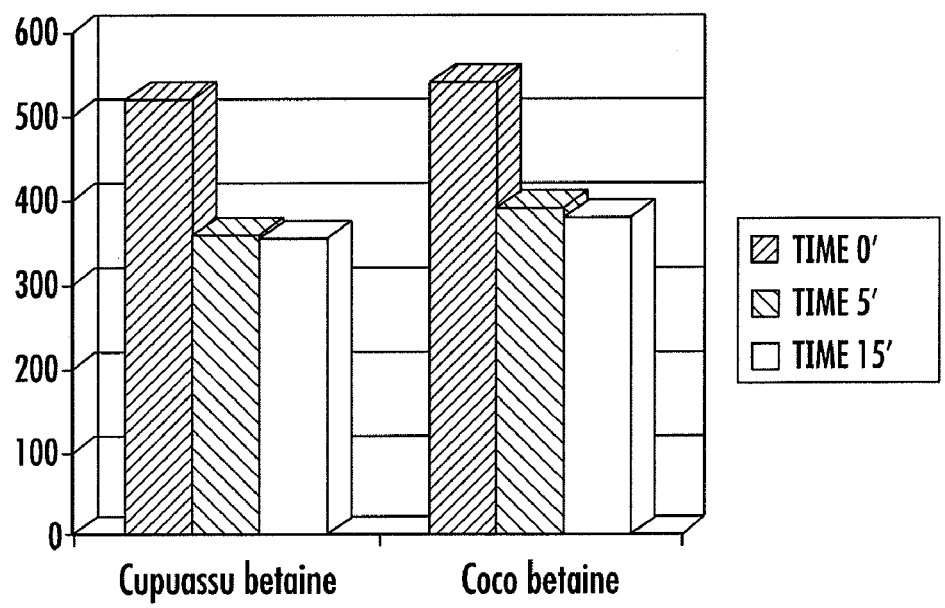
FIG. 2 is a bar graph comparing the difference in foam volume for the two shampoo formulations of FIG. 1.

The results of these measurements are shown in FIG. 2 and demonstrate the equality of both shampoos with regard to foam leveling which foam Volume in ml after 0, 5 and 15 Minutes is compared.

Viscosity Increasing Effect

Figure 3:
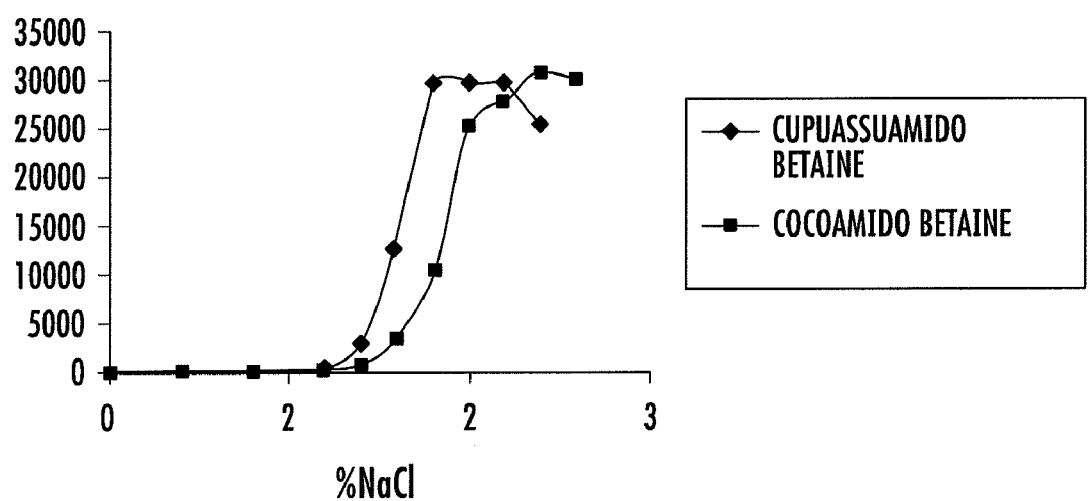
FIG. 3 depicts viscosity curves of different betaines.

FIG. 3 depicts viscosity curves of different betaines and shows the viscosity increasing effect of the amidoamines of the present invention. In direct comparison to cocamido propyl betaine less NaCl has to be used in order to thicken the composition.

Irritation Tests a) HET-CAM Methodology

Amidoamines according to the invention were tested against Cocamido propyl betaine in a simultaneous skin and eye irritation test in vitro according to HET-CAM methodology (Table 1).

Method Description:

On the experiment day, the leghorn chicken eggs, which were incubated at 37° C. and assessed after 10 days of fertilisation with a weight between 50 and 65 g), were carefully opened by means of scissor cuts in the air pocket region under a halogen lamp. The cavity was humidified with a saline solution at 37° C. to remove the external membrane with tongs. The test sample, 300 μl, was placed over a chorion-allantoid membrane for 20 seconds and washed in the saline solution. The hyperemia, hemorrhage, thrombosis or opacity reactions were observed visually for a total period of 5 minutes. The phenomena observed vary according to the irritation intensity of the samples which are classified according to the following scores (Tables 2 and 3).

TABLE 1

In vitro evaluation of surfactant bases containing Cocamido propyl betaine (CAPB), Sodium Laureth Sulfate (SLES) or Cuppuassu amido propyl betaine (CupAPB).

| Surfactant Base (% active substance) | Score 1 | Score 2 | Score 3 | Score 4 | Medium | SD |
|---|---|---|---|---|---|---|
| SLES (7.10%) | 15 | 15 | 15 | 15 | 15 | 0 |
| SLES (7.10%) + CAPB (2.66%) | 15 | 15 | 15 | 15 | 15 | 0 |
| SLES (7.10%) + CupAPB (2.66%) | 8 | 10 | 10 | 10 | 9.5 | 1 |
| SLES (7.10%) + CAPB (2.04%) | 10 | 15 | 15 | 15 | 13.8 | 2.5 |
| SLES (7.10%) + CupAPB (2.04%) | 8 | 8 | 10 | 10 | 9 | 1.2 |
| SLES (7.10%) + CAPB (1.63%) | 13 | 17 | 17 | 17 | 16 | 2 |
| SLES (7.10%) + CupAPB (1.63%) | 10 | 10 | 10 | 10 | 10 | 0 |
| SLES (7.10%) + CAPB (1.23%) | 12 | 10 | 10 | 10 | 10.5 | 1 |
| SLES (7.10%) + CupAPB (1.23%) | 10 | 10 | 10 | 10 | 10 | 0 |

TABLE 2

| Phenomenon | Time | | |
|---|---|---|---|
| | t ≤ 30 s | 30 < t ≤ 2 min | 2 min < t ≤ 5 min |
| Hyperemia | 5 | 3 | 1 |
| Hemorrhage | 7 | 5 | 3 |
| Coagulation | 9 | 7 | 5 |

TABLE 3

| Scores | Classification |
|---|---|
| Medium Score < 1 | practically not irritating |
| 1 ≤ Medium Score < 5 | slightly irritating |
| 5 ≤ Medium Score < 9 | moderately irritating |
| Medium Score ≥ 9 | irritating |

The results show that there is a synergistic effect of Cupuassuamido propyl betaine and Sodium Lauryl ether sulfate, even in different concentrations.

b) Toxicological Profile in Animals

The toxicological profile of the Cupuassuamido propyl betaine was compared to Cocamido propyl betaine. The results in table 4 show that the Cupuassuamido propyl betaine is less irritant than the standard Cocamidopropyl betaine.

TABLE 4

| | Toxicological profile in animals | |
|---|---|---|
| Test | Cupuassuamido propyl betaine | Cocamido propyl betaine |
| Ocular Irritability | Not irritating | Moderately irritating |
| Primary Dermic Irritation | Not irritating | Minimum irritating |
| Cumulative Dermic Irritation | Minimum irritating | Moderately irritating | c) Red Blood Cell Test

The Red Blood Cell Test (RBC) was carried out with the combination of Sodium Lauryl Ether Sulfate (SLES) and Cupuassuamido Propyl Betaine (CupAPB) or Sodium Lauryl Ether Sulfate (SLES) and Cocamido Propyl Betaine (CAPB) in different concentrations. The test was performed according to "Standardization of an in vitro Red Blood Cell Test for Evaluating the Acute Cytotoxic Potential of Tensides" (W. J. W. Pape and U. Hoppe, Drug Res. 40(I):4, 1990). The results are shown in Table 5.

TABLE 5

| | Red Blood Cell Test | | |
|---|---|---|---|
| Surfactant Base (% active substance) | hemolysis (H) | oxidation (O) | H/O |
| SLES (7.10) | 275.0 | 16.10 | 17.1 |
| SLES (7.10) + CAPB (2.66) | 220.0 | 3.56 | 61.8 |
| SLES (7.10) + CupAPB (2.66) | 230.0 | 3.37 | 68.2 |
| SLES (7.10) + CAPB (2.04) | 190.9 | 5.1 | 37.6 |
| SLES (7.10) + CupAPB (2.04) | 200.0 | 4.74 | 42.2 |
| SLES (7.10) + CAPB (1.63) | 232.0 | 5.5 | 42.3 |
| SLES (7.10) + CupAPB (1.63) | 150.0 | 1.05 | 143.7 |
| SLES (7.10) + CAPB (1.23) | 309.0 | 5.7 | 54.5 |
| SLES (7.10) + CupAPB (1.23) | 204.1 | 3.8 | 53.5 |

The PBC test results demonstrate that the Cupuassuamido propyl betaine decreases the hemolysis and oxidation of proteins caused by Sodium Lauryl Ether Sulfate.

Cosmetic Compositions

Formulation 1. Cosmetic Composition for hair (Shampoo)

| Component | % |
|---|---|
| Guar Hydroxypropyl Trimonium | 0.05-1.00 |
| Citric acid | q.s. |
| NaCl | q.s. |
| Sodium Laureth Sulfate | 15.0-40.0 |
| Sodium Laureth Carboxylate | 0.1-6.00 |
| Cupuassuamidopropyl Betaine | 1.00-20.00 |
| Decyl glucoside | 1.00-6.00 |
| Sequestrant | q.s. |
| Glycol Distearate | 0.50-3.00 |
| Ethoxylated Vegetable Oil | 1.00-5.00 |
| Preservative | q.s. |
| Fragrance | q.s. |
| Antioxidant | q.s. |
| Triethanolamine | q.s. |
| Pigments | q.s. |
| Water | Up to 100.00 |

Formulation 2. Cosmetic composition for body cleansing (Shower gel)

| Component | % |
|---|---|
| Carbomer | 0.1-1.50 |
| NaCl | q.s. |
| Sodium Laureth Sulfate | 15.0-35.0 |
| Cupuassuamidopropyl Betaine | 2.0-20.0 |
| Decyl Glucoside | 1.00-6.00 |
| Sequestrant | q.s. |
| Ethoxylated Vegetable Oil | 1.00-5.00 |
| Preservative | q.s. |
| Fragrance | q.s. |
| Antioxidant | q.s. |
| Triethanolamine or citric acid | q.s. |
| Pigments | q.s. |
| Water | Up to 100.00 |

Formulation 3. Cosmetic composition for body cleansing (bar soap)

| Component | % |
|---|---|
| NaCl | q.s. |
| Soap fatty esters | 80.0-99.0 |
| Cupuassuamidopropyl Betaine | 0.50-20.0 |
| Decyl Glucoside | 1.00-6.00 |
| Sequestrant | q.s. |
| Glycerin | 0.1-15.00 |
| Vegetable Oil/Mineral Oil | 0.10-30.00 |
| Preservative | q.s. |
| Fragrance | q.s. |
| Antioxidant | q.s. |
| Triethanolamine or citric acid | q.s. |
| Pigments | q.s. |
| Titanium Dioxide | q.s. |
| Optical Whitenner | q.s. |
| Water | Up to 100.00 |

Formulation 4. Cosmetic composition for face cleansing (face liquid soap)

| Component | % |
|---|---|
| NaCl | q.s. |
| Sodium Laureth Sulfate | 10.0-40.0 |
| Sodium Tridecyl Sulfate | 1.0-15.0 |
| Cupuassuamidopropyl Betaine | 1.0-20.0 |

Formulation 4. Cosmetic composition for face cleansing (face liquid soap)

| Component | % |
|---|---|
| Decyl Glucoside | 1.00-6.00 |
| EDTA Dissodium | 0.10 |
| Preservative | q.s. |
| Fragrance | q.s. |
| Antioxidant | q.s. |
| Triethanolamine or citric acid | q.s. |
| Pigments | q.s. |
| Water | Up to 100.00 |

The invention claimed is:

1. A cosmetic composition comprising a mixture of compounds having the general formula (I)

$$R^1—CONH—X—NR^2R^3—R^4\text{-y} \quad (I)$$

in which $R^1$ represents an alkyl or alkenyl moiety containing 11 to 21 carbon atoms, X stands for a $(CH_2)_n$— group and n is an integer from 1 to 6, $R^2$ and $R^3$ independently represent an alkyl moiety with 1 to 4 carbon atoms or an hydrogen atom, $R^4$ is a $C_1$-alkylene, and Y stands for a COO— group, and wherein the compound of formula (I) is prepared by reacting the oil from Theobroma grandiflorum comprising a mixture of fatty acids in the following distribution: about 0.0-1% myristic acid, about 5.0-10.0% palmitic acid, about 25-35% stearic acid, about 30-50% oleic acid, about 2-5% linoleic acid, abut 0.0-1% linolenic acid, about 10-15% arachidonic acid and about 0.0-3% behenic acid with an amine of the formula (II)

$$H_2N—X—NR^2R^3 \quad (II)$$

and subsequently reaction with sodium monchloracetate, and wherein the compound of formula (I) is present in a cosmetic composition.

2. The cosmetic composition of claim 1, characterized in that the mixture of compounds of formula (I) $R^2$ is identically to $R^3$.

3. The cosmetic composition of claim 1, characterized in that the compounds of formula (I) $R^2$ and $R^3$ represent a methyl group.

4. The cosmetic composition of claim 1, characterized in that X in formulas (I) and (II) represents a $(CH_2)_3$-group.

5. The cosmetic composition of claim 1, characterized in that the cosmetic composition contains 0.1 to 20% by weight of the mixture of compounds of formula (I).

6. The cosmetic composition of claim 1, characterized in that $R^4$ is $(CH_2)n$ wherein n is a number of 1 to 2.

7. The cosmetic composition of claim 2, characterized in that $R^4$ is $(CH_2)n$ wherein n is a number of 1 to 2.

8. The cosmetic composition of to claim 3, characterized in that $R^4$ is $(CH_2)n$ wherein n is a number of 1 to 2.

9. The cosmetic composition of claim 4, characterized in that $R^4$ is $(CH_2)n$ wherein n is a number of 1 to 2.

10. The cosmetic composition of claim 5, characterized in that $R^4$ is $(CH_2)n$ wherein n is a number of 1 to 2.

11. A process for preparing compounds of general formula (1) as defined in claim 1, the process comprising the steps of:
(i) reacting the oil from Theobroma grandiflorum with dimethylaminopropyl amine in a temperature range of from 140° C. up to 210° C. for approximately four hours;
(ii) washing the resulting amidoamide to eliminate any excess amine; and
(iii) reacting the resulting amidoamide with a quaternizing compound, by adding the amidoamine to the quaternizing compound in an aqueous solution at 80-85° C. for three hours, and maintaining the pH at a value between 8 and 9.

12. A process according to claim 11, wherein the quaternizing compound is sodium monochloroacetate.

13. A process according to claim 11, wherein step (iii) takes place under weakly alkaline conditions.

14. A process for preparing compounds having the general formula (I)

$$R^1—CONH—X—NR^2R^3—R^4\text{-y} \quad (I)$$

in which $R^1$ represents an alkyl or alkenyl moiety containing 11 to 21 carbon atoms, X stands for a $(CH_2)_n$— group and n is an integer from 1 to 6, $R^2$ and $R^3$ independently represent an alkyl moiety with 1 to 4 carbon atoms or an hydrogen atom, $R^4$ is a group derived from a quaternizing compound, and Y stands for a COO— group, wherein the compound of formula (I) is prepared by:
(i) reacting the oil from Theobroma grandiflorum with dimethylaminopropyl amine in a temperature range of from 140° C. up to 210° C.;
(ii) washing the resulting amidoamide to eliminate any excess amine; and
(iii) reacting the resulting amidoamide with a quaternizing compound in an aqueous solution at 80-85° C. for three hours.

* * * * *